United States Patent
Sabahi

(10) Patent No.: US 9,796,939 B2
(45) Date of Patent: Oct. 24, 2017

(54) MULTI-RING ANTIOXIDANTS WITH ANTIWEAR PROPERTIES

(71) Applicant: SI Group, Inc., Schenectady, NY (US)

(72) Inventor: Mahmood Sabahi, Baton Rouge, LA (US)

(73) Assignee: SI GROUP, INC., Schenectady, NY (US)

( * ) Notice: Subject to any disclaimer, the term of this patent is extended or adjusted under 35 U.S.C. 154(b) by 383 days.

(21) Appl. No.: 14/048,560

(22) Filed: Oct. 8, 2013

(65) Prior Publication Data

US 2014/0038871 A1 Feb. 6, 2014

Related U.S. Application Data

(62) Division of application No. 13/003,745, filed as application No. PCT/US2009/050410 on Jul. 13, 2009, now Pat. No. 8,580,718.

(60) Provisional application No. 61/082,446, filed on Jul. 21, 2008.

(51) Int. Cl.

| | | |
|---|---|---|
| *C10M 135/30* | (2006.01) | |
| *C10L 1/24* | (2006.01) | |
| *C07C 323/18* | (2006.01) | |
| *C09K 15/14* | (2006.01) | |
| *C09K 15/28* | (2006.01) | |
| *C07C 319/20* | (2006.01) | |
| *C07C 319/22* | (2006.01) | |

(52) U.S. Cl.
CPC .......... *C10L 1/2412* (2013.01); *C07C 323/18* (2013.01); *C09K 15/14* (2013.01); *C09K 15/28* (2013.01); *C10M 135/30* (2013.01); *C07C 319/20* (2013.01); *C07C 319/22* (2013.01); *C10M 2219/087* (2013.01); *C10N 2230/04* (2013.01); *C10N 2230/10* (2013.01)

(58) Field of Classification Search
CPC ..... C10L 1/2412; C07C 323/18; C09K 15/14; C09K 15/28; C10M 135/30; C10M 2219/087; C10N 2230/04; C10N 2230/10
See application file for complete search history.

(56) References Cited

U.S. PATENT DOCUMENTS

| | | |
|---|---|---|
| 3,311,663 A | 3/1967 | Degeorges et al. |
| 3,489,804 A | 1/1970 | O'Shea |
| 3,673,091 A | 6/1972 | Werzner et al. |
| 3,843,614 A | 10/1974 | Doorakian |
| 4,163,729 A | 8/1979 | Adams |
| 4,912,249 A | 3/1990 | Kupper et al. |
| 4,946,610 A | 8/1990 | Lam et al. |
| 6,096,695 A * | 8/2000 | Lam ............... C07C 319/14 252/404 |
| 2006/0128574 A1 | 6/2006 | Dong et al. |

FOREIGN PATENT DOCUMENTS

| | | |
|---|---|---|
| EP | 0257968 A2 | 3/1988 |
| EP | 0811631 A2 | 10/1997 |
| JP | 4702294 B4 | 10/1972 |
| JP | 10-097075 A | 4/1998 |
| SU | 391124 A | 12/1973 |
| WO | 90/14397 A1 | 11/1990 |
| WO | 97/44310 A1 | 11/1997 |

OTHER PUBLICATIONS

Paushkin, Ya. M.; Glushkova, L. V.; Skripko, L. A.; Volkotrub, M. N., Synthesis of sterically-hindered hexaphenols, Inst. Fiziko-Org. Khim., Minsk, USSR, Vestsi Akademii Navuk BSSR, Seryya Khimichnykh Navuk (1975), (2), 48-50 CODEN: VBSKAK; ISSN: 0002-3590.*
ScienceDirect Abstract of Liu, Y., et al., "Temperature-controlled selective reduction of arenesulfonyl chlorides promoted by samarium metal in DMF", Tetrahedron Letters, vol. 44(22), May 2003, pp. 4291-4294. 1 Page.
Ma, D., et al., "N,N-Dimethyl Glycine-Promoted Ullmann Coupling Reaction of Phenols and Aryl Halides", Organic Letters, vol. 5(21), 2003, pp. 3799-3802.
Benda et al., "Synthetics Basics Polyalphaolefins-Base Fluids for High-Performance Lubricants", Journal of Syntheti Lubrication 13:41-57 (1996).
Pinchart, A., et al., "Functionalized p-Phenylene Sulfides Synthesis of New Molecular Wires", Tetrahedron Letters, 39, 1998, pp. 543-546.
Takeuchi, D., et al., "Synthesis and Structure of Cyclic Oligo(p-phenylene oxide)s, . . . ", J. Org. Chem., vol. 71,2006, pp. 8614-8617.
Vincente, J., et al., "A New Approach to the Synthesis of Oligomers. Application to the synthesis of p-phenylene thioether wires", Tetrahedron Letters, vol. 46, 2005, pp. 5839-5840.

* cited by examiner

*Primary Examiner* — Taiwo Oladapo
(74) *Attorney, Agent, or Firm* — Jeffrey N. Townes; LeClairRyan

(57) ABSTRACT

Described are multi-ring antioxidant products comprising at least one sulfur-bridged aromatic hydrocarbon compound substituted on at least one of its aromatic rings by at least one sterically hindered 3,5-dihydrocarbyl-4-hydroxybenzyl moiety. Such products have the formula:

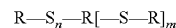

wherein each R is, independently, an aromatic hydrocarbon group having 6-12 carbon atoms, wherein m is 0-20, wherein n is 1-6 when m is 0, and when n is 1, m is 1-20; and wherein at least one of R, $R^1$, and $R^2$ is substituted by at least one such sterically hindered moiety. The preparation of such products and their use as antioxidants in compositions normally susceptible to oxidative degradation in oxygen or air, e.g., liquid fuel and lubricants, are also described.

11 Claims, No Drawings

MULTI-RING ANTIOXIDANTS WITH ANTIWEAR PROPERTIES

REFERENCE TO RELATED APPLICATIONS

This application is a divisional of U.S. patent application Ser. No. 13/003,745, filed Jan. 11, 2011, now allowed, which is the National Stage of International Patent Appl. No. PCT/US2009/050410, filed on Jul. 13, 2009, which in turn claims the benefit of U.S. Provisional Patent Appl. No. 61/082,446, filed on Jul. 21, 2008, the disclosures of which are incorporated herein by reference.

TECHNICAL FIELD

This invention relates to novel multi-ring compounds and product mixtures having antioxidant and antiwear properties, their preparation, and their uses.

BACKGROUND

It is well known that a wide variety of organic materials are susceptible to oxidative degradation in the presence of air or oxygen, especially when at elevated temperatures. Such organic materials include, for example, gasolines, diesel fuels, burner fuels, gas turbine and jet fuels, automatic transmission fluids, gear oils, engine lubricating oils, thermoplastic polymers, natural and synthetic rubber, and the like. Over the years, considerable efforts have been devoted to discovery and development of compounds capable of minimizing the degradation of one or more of such materials. As conditions of use and exposure of such materials to various oxygen containing environments change over the years, the desire for new effective oxidation inhibitors (a.k.a. antioxidants) continues.

The oxidation of oils and lubricants during use serves as one example of this trend of change over the years. Although it has been long known that oils and lubricants oxidize during use leading to the formation of organic acids and other deleterious oxygenated products, the increasing complexity of modern automotive engines and various high speed machinery and their general requirements for improved performance and less frequent maintenance has resulted in a vital need for new effective oxidation inhibitors capable of functioning effectively under these changing conditions. For many lubricant applications, new antioxidants capable of functioning at elevated temperatures and also possessing antiwear properties would be a welcome contribution.

This invention addresses the foregoing problems and needs.

BRIEF NON-LIMITING SUMMARY OF THE INVENTION

Pursuant to this invention, among other things, new compounds and new mixtures of compounds are provided. These compounds and mixtures of compounds are multi-ring compounds comprising at least one sulfur-bridged aromatic hydrocarbon compound substituted on at least one of the aromatic rings thereof by at least one sterically hindered 3,5-dihydrocarbyl-4-hydroxybenzyl moiety. A typical group of such compounds can be depicted by formula (I) as follows:

(I)

wherein each R is, independently, an aromatic group having in the range of 6 to about 24 carbon atoms, wherein m is a number in the range of 0 to about 20, wherein n is a number in the range of 1 to about 6, preferably 1 to 3, and more preferably 1 to 2, when m is 0, and wherein m is in the range of 1 to about 20 when n is 1; and wherein at least one R in the above formula is substituted by at least one sterically hindered 3,5-dihydrocarbyl-4-hydroxybenzyl moiety. It can be seen from the above formula that these new compounds contain in the molecule (i) one or more sterically hindered phenolic moieties and (ii) at least one aromatically bonded sulfur atom. Preferably, R is an aromatic hydrocarbon group. However, R can be substituted by various groups, including functional groups, which do not interfere with the production of compounds of formula (I). Such substituent groups are discussed in connection with formula (III) hereinafter.

For convenience, the multi-ring sulfur-bonded aromatic compounds of this invention, whether in the form of (i) individual isolated compounds, (ii) mixtures of two or more isolated individual compounds, or (iii) mixtures comprised of products formed by reaction of reactants (a) and (b) and which mixtures after work-up of the reaction product mixture contain no more than about 1 wt % of reaction solvent and catalyst residues, are often referred to hereinafter either as compound of this invention or compounds of this invention, depending upon the context.

Because of their makeup, the compounds of this invention are deemed to be effective in inhibiting premature oxidative deterioration of substances normally susceptible to oxidative degradation over time during use or storage. In addition, these new multi-ring compounds are deemed to serve as antioxidants at elevated temperatures and to contribute antiwear properties to lubricants such as gear oils, transmission fluids, engine oils, and in general, to lubricants operating under friction-producing, heavy-duty, or extreme pressure conditions. This invention thus also provides lubricants and other substances normally susceptible to oxidative degradation in the presence of air or oxygen during use or storage, especially at elevated temperatures, with which have been blended or otherwise incorporated these new multi-ring compounds or products. Also provided by this invention is a process of blending antioxidant quantities and/or antiwear quantities of the compounds of this invention with substances normally susceptible to oxidative degradation over time, especially when at elevated temperatures, and more especially when operating under friction-producing or extreme pressure conditions.

The compounds of this invention can be produced by a process which comprises bringing together in a liquid reaction medium:

a) at least one compound of formula (II) as follows:

(II)

wherein each R is, independently, an aromatic hydrocarbon group having in the range of 6 to about 24 carbon atoms, wherein m is a number in the range of 0 to about 20, wherein n is a number in the range of 1 to about 6, preferably 1 to 3, and more preferably 1 to 2, when m is 0, and wherein m is in the range of 1 to about 20 when n is 1; and b) at least one sterically hindered 2,6-dihydrocarbylphenol having in its 4-position a methoxymethyl group, a carboxymethyl group, or a hydroxymethyl group;

in the presence of an acidic alkylation catalyst.

For reaction to take place, the reaction medium will of course be at a temperature at which formation of the desired compound or compounds of this invention occurs. Typically, temperatures in the range of about 20 to about 120° C. are suitable.

Preferred as reactant (b) are 2,6-di-tert-butyl-4-methoxymethylphenol and 2,6-di-tert-butyl-4-acetoxyphenol (also called 3,5-di-tert-butyl-4-hydroxybenzylacetate) because of the ease with which they can be produced and the high yields of desired products achievable by their use pursuant to this invention.

The ensuing description and appended claims still further illustrate and describe this invention.

FURTHER DETAILED DESCRIPTION OF THE INVENTION

It can be seen that the compounds of this invention are either monomeric or oligomeric in character. Thus referring to formula (I), when m is zero the product basically comprises monomeric diarylsulfides having 1 to 6 sulfur atoms in the bridge between the two aryl groups, and at least one of which aryl groups is substituted by at least one sterically hindered 3,5-dihydrocarbyl-4-hydroxybenzyl moiety. Of these compounds, diarylsulfides having 1 to 3 sulfur atoms in the bridge between the two aryl groups, at least one of which aryl groups is substituted by at least one sterically hindered 3,5-dihydrocarbyl-4-hydroxybenzyl moiety are preferred because they have higher solubility in organic solvents, including oils of lubricating viscosity than corresponding products having 4, 5, or 6 sulfur atoms in the bridge. Typically, individual molecules of such substituted diarylsulfide product mixtures will have up to about 4 such sterically hindered 3,5-dihydrocarbyl-4-hydroxybenzyl moieties as ring substituents. The substituted diarylsulfide product mixtures of this invention as formed will typically comprise some unsubstituted diarylsulfides, some monosubstituted diarylsulfides, some disubstituted diarylsulfides, and some trisubstituted diarylsulfides, such substitution being made up of sterically hindered 3,5-dihydrocarbyl-4-hydroxybenzyl moieties. It is contemplated that some tetrasubstituted, some pentasubstituted, and some hexasubstituted diarylsulfides may be produced using excess amounts of compound b) and elevated temperatures during their synthesis.

While further variations are possible, in many cases the aromatic hydrocarbon groups, R in formula (I) will have, independently, a total of 6, 10, or 12 ring carbon atoms. One or more of such aromatic hydrocarbon groups in an individual compound of formula (I) will be substituted by at least one sterically hindered 3,5-dihydrocarbyl-4-hydroxybenzyl moiety. Additionally, all or some of such hydrocarbon groups can be substituted by short chain (i.e., $C_{1-4}$) alkyl groups. However, from the standpoint of availability and ease of preparation, the aromatic rings, R, are preferably 6-membered benzene rings free of alkyl substitution.

The compounds of this invention, when in the form of mixtures of two or more individual compounds of formula (I), which mixtures can be formed by mixing together isolated individual compounds of formula (I), can be in any proportions relative to each other.

When in the form of preferred mixtures comprised of products formed by reaction of reactants (a) and (b) from which reaction solvent and catalyst residues have been at least substantially entirely removed, the individual components of the compounds of this invention can also be in varied proportions relative to each other. For example, when using a suitably large molar excess of reactant (a), mixtures can be produced in which the amount of compound(s) of formula (I) substituted by one sterically hindered 3,5-dihydrocarbyl-4-hydroxybenzyl moiety is the major product formed in the reaction. When using reactant (a) and (b) in other proportions, typically a mixture is formed in which mono-, di-, and trisubstitution by 3,5-dihydrocarbyl-4-hydroxybenzyl moieties are the major components of the mixture and tetra-, penta-, and hexa-substitution by 3,5-dihydrocarbyl-4-hydroxybenzyl are the minor components of the product mixture.

Presently preferred mixtures of compounds of formula (I) are those in which the relative proportions of compound(s) of formula (I) are as follows:

1) about 10 to about 50 wt % of compound(s) of formula (I) with one sterically hindered 3,5-dihydrocarbyl-4-hydroxybenzyl moiety in the molecule,
2) about 20 to about 70 wt % of compound(s) of formula (I) with two sterically hindered 3,5-dihydrocarbyl-4-hydroxybenzyl moieties in the molecule,
3) about 5 to about 40 wt % of compound(s) of formula (I) with three sterically hindered 3,5-dihydrocarbyl-4-hydroxybenzyl moieties in the molecule,
4) about 1 to about 20 wt % of compound(s) of formula (I) with four sterically hindered 3,5-dihydrocarbyl-4-hydroxybenzyl moieties in the molecule,
5) balance to 100 wt % comprising unsubstituted reactant (a) and/or other reaction products.

Of the monomeric compounds of this invention, those of formula (I) in which m is 0 and n is in the range of 1 to 3 are preferred because of ease of synthesis, with those in which n is 1 being even more preferred for this reason.

Of the oligomeric compounds of this invention, those of formula (I) in which m is in the range of 1 to 20 and n is 1 are preferred from the standpoint of ease of synthesis.

From the standpoint of usefulness as antioxidants and antiwear agents in oils of lubricating viscosity, compounds of this invention which are in the liquid state at one or more temperatures below 100° C. are preferred, as they can be readily blended with the oils.

Preferred compounds of this invention are those of formula (I) having a solubility in most organic solvents of at least 10 grams per liter at 25° C. and that (i) is in the liquid state at 25° C., or (ii) is a solid at 25° C. and has a melting point below about 100° C.

As can be seen from formula (I), the compounds of this invention, whether in the form of individual compound or mixtures of two or more such compounds, can range widely in structure. They can be formed by reaction between (a) at least one arylsulfide ($RS_nR$) or poly(arylsulfide) (R—S—[R—$S_n$—]$_m$R) where n is 1 to 6, preferably 1 to 3, and more preferably 1, and m is as defined in formula (I), and (b) at least one sterically hindered 2,6-dihydrocarbylphenol having in its 4-position a methoxymethyl group (—$CH_2OCH_3$), an acetoxymethyl group (—$CH_2OC(=O)CH_3$ or a hydroxymethyl group (—$CH_2OH$). Some or all of the aromatic rings in the compounds of this invention can carry inert substituents such as saturated hydrocarbyl groups.

Reactant (a)

Reactant (a) can be one or more diarylsulfides. Such compounds can be depicted by the formula:

R—(S)$_n$—R (III)

wherein the R groups can be the same or different and are aryl groups which can be either unsubstituted or substituted by one or more substituents selected from among inert hydrocarbyl, alkoxy, aryloxy, alkylthio, halo, amino, alkyl amino, or aryl amino (i.e., substituent groups which do not interfere with the reaction which forms the compounds of this invention). Each of the R groups typically contains, independently, in the range of 6 to about 24 carbon atoms and from 1 to 3 aromatic rings, which can be fused aromatic rings or non-fused aromatic rings. In the above formula, n is a number which can be in the range of 1 to about 6, and preferably is in the range of 1 to 3, more preferably in the range of 1 to 2, and still more preferably, n is 1. Mixtures of two or more arylsulfides of the above Formula (III) can be used in preparing the compounds of this invention.

The aromatic ring systems of the diarylsulfides can vary. For example, they can be phenyl, 1-naphthyl, 2-naphthyl, 2-biphenylyl, 3-biphenylyl, 4-biphenylyl, anthryl, dihydronaphthyl, tetrahydronaphthyl, phenyl-substituted biphenylyl groups, and other analogous aryl hydrocarbon groups. Preferably they are phenyl groups.

Preferred arylsulfides for use in preparing the compounds of this invention are diaryl monosulfides or diaryl disulfides in which the two aryl groups are two phenyl groups which may contain one or more $C_{1-4}$ alkyl and more preferably $C_{1-2}$ alkyl, and still more preferably, methyl substituents, with the proviso that at least one of the phenyl groups of such diarylsulfide reactant has at least one of its ring carbon atoms unsubstituted and sufficiently unhindered by adjacent substituents as to enable alkylation by reactant (b).

Non-limiting examples of some of the various suitable diarylsulfides for use as reactant (a) include: diphenyl monosulfide; phenyl-2-methylphenyl monosulfide; phenyl-3-methylphenyl monosulfide; phenyl-4-methylphenyl monosulfide; phenyl-2-ethylphenylmono-sulfide; phenyl-3-ethylphenyl monosulfide; phenyl-4-ethylphenyl monosulfide; phenyl-4-butylphenylmono-sulfide; phenyl-2,6-dimethylphenyl monosulfide; bis(2-methylphenyl) monosulfide; bis(3-methylphenyl) monosulfide; bis(4-methylphenyl) monosulfide; bis(2-ethylphenyl) mono-sulfide; bis(3-ethylphenyl) monosulfide; bis(4-ethylphenyl) monosulfide; bis(4-butylphenyl) monosulfide; bis(2,6-dimethylphenyl) monosulfide; (2-methylphenyl)(4-methylphenyl) monosulfide; (4-hexylphenyl)(2-methylphenyl) monosulfide; (biphenylyl)-(phenyl) monosulfide; bis(biphenylyl) monosulfide; bis(1-naphthyl) monosulfide; bis(2-napthyl) monosulfide; (2-naphtyl)(phenyl) monosulfide; diphenyl disulfide; phenyl-2-methylphenyl disulfide; phenyl-3-methylphenyl disulfide; phenyl-4-methylphenyl disulfide; phenyl-2-ethylphenyl disulfide; phenyl-3-ethylphenyl disulfide; phenyl-4-ethylphenyl disulfide; phenyl-4-butylphenyl disulfide; phenyl-2,6-dimethylphenyl disulfide; bis(2-methylphenyl)disulfide; bis(3-methylphenyl)disulfide; bis(4-methylphenyl)disulfide; bis(2-ethylphenyl)disulfide; bis(3-ethylphenyl)disulfide; bis(4-ethylphenyl)disulfide; bis(4-butylphenyl)disulfide; bis(2,6-dimethylphenyl)disulfide; (2-methylphenyl)(4-methylphenyl)disulfide; (4-hexylphenyl)(2-methylphenyl)disulfide; bis(biphenylyl)disulfide; bis (1-naphthyl)disulfide.

Analogs of the above compounds in which there are an average of at least about 3 sulfur atoms per molecule (e.g., in the range of about 3 to 5 sulfur atoms per molecule) constitute further examples of suitable substances for use as reactant (a).

Alternatively, reactant (a) can be one or more poly(arylsulfides). Such compounds can be depicted by the formula:

$$R\text{—}(S\text{—}R)_m \qquad (IV)$$

wherein the R groups can be the same or different and can be substituted or unsubstituted, and are as defined above in connection with formula (III), and m is a number in the range of 2 to about 20. When reactant (a) is a mixture of compounds, m can be a fractional number constituting the average of the mixture. Otherwise, m is a whole number. As in the case of the compounds of formula (III), when substituted the substituents on some or all of the aryl groups, R, can be substituted by one or more substituents selected from among inert hydrocarbyl, alkoxy, hydroxy, aryloxy, alkylthio, halo, amino, alkyl amino, or aryl amino (i.e., substituent groups which do not interfere with the reaction which forms the compounds of this invention). Each of the R groups typically contains, independently, in the range of 6 to about 24 carbon atoms and from 1 to 3 aromatic rings, which can be fused aromatic rings or non-fused aromatic rings. Preferably, each R is a phenyl group or a substituted phenyl group. More preferably, each R is an unsubstituted phenyl group. Mixtures of two or more poly(arylsulfides) of the above formula (IV) can be used in preparing compounds of this invention.

Mixtures of one or more compounds of each of formulas (III) and (IV) can also be used in preparing compounds of this invention.

Methods of preparing, or that can be adapted for preparing, suitable aromatic sulfur-containing compounds of formulas (II), (III), and (IV) are known and reported in the literature. See, for example, Alain Pinchart, et al., *Tetrahedron Letters*, Volume 39, pages 543-546, 1998; and J. Vincente, et al., *Tetrahedron Letters*, Volume 46, pages 5839-5440, 2005.

Reactant (b)

Reactant (b) is at least one sterically hindered 2,6-dihydrocarbylphenol having in its 4-position a methoxymethyl group ($-CH_2OCH_3$), a carboxymethyl group ($-CH_2C(=O)CH_3$), or a hydroxymethyl group ($-CH_2OH$). The steric hindrance is preferably achieved by having as at least one of the dihydrocarbyl groups in the 2-position, a tertiary alkyl group having up to about 8 carbon atoms.

It will be understood and appreciated that whether reactant (b) is a sterically hindered 2,6-dihydrocarbylphenol having in its 4-position a methoxymethyl group, or a carboxymethyl group or a hydroxymethyl group, and where, in each case, the hydrocarbyl substituents in the 2- and 6-positions are the same, the resultant substituted compound or compounds of this invention will have the same 3,5-dihydrocarbyl-4-hydroxybenzyl substituent(s). In other words, the ($-CH_2OCH_3$) group in the 4-position, the ($-CH_2C(=O)CH_3$) group in the 4-position, or the ($-CH_2OH$) group in the 4-position of the sterically hindered phenol will, in the reaction, result in the formation of 3,5-dihydrocarbyl-4-hydroxybenzyl substitution on aromatic rings of the compound or compounds of this invention. It will also be understood that not all of the aromatic rings of the compound or compounds of this invention need be substituted by a 3,5-dihydrocarbyl-4-hydroxybenzyl substituent. Thus, in a single substituted diarylsulfide compound of this invention, only one 3,5-dihydrocarbyl-4-hydroxybenzyl substituent in the molecule is sufficient, and if the substituted diarylsulfide of this invention is a mixture of such compounds, it is not necessary that all of the molecules of the mixture be substituted by a 3,5-dihydrocarbyl-4-hydroxybenzyl group. Usually, at least 5-95% of the molecules of such a mixture will be substituted by at least one 3,5-dihydrocarbyl-4-hydroxybenzyl substituent. Preferably, at least 20-60% of the molecules of such a mixture will be substituted by at least one 3,5-dihydrocarbyl-4-hydroxybenzyl substituent, and more preferably at least 20-40% will be substituted by one 3,5-dihydrocarbyl-4-hydroxybenzyl substituent. Similar considerations apply to single substituted poly(arylsulfides) of this invention and mixtures of substituted poly(arylsulfides) of this invention. Thus, in a single substituted poly (arylsulfide) compound of this invention, or in a mixture of substituted poly(arylsulfide) compounds of this invention, substitution by at least one 3,5-dihydrocarbyl-4-hydroxybenzyl substituent per molecule will provide some antioxidant and antiwear activity. Usually, at least 10-95% of the molecules of such a mixture will be substituted by at least one 3,5-dihydrocarbyl-4-hydroxybenzyl substituent. Preferably, at least 20-62% of the molecules of such a mixture will be substituted by at least one 3,5-dihydrocarbyl-4-hydroxybenzyl substituent and more preferably by 20-40% of such a mixture will be substituted by at least one 3,5-dihydrocarbyl-4-hydroxybenzyl substituent.

The hydrocarbyl groups in the ortho positions relative to the phenolic hydroxyl group of reactant (b) can vary provided that the resultant steric hindrance is sufficient to provide acceptable antioxidant performance. Typically, one of such hydrocarbyl substituents is a tertiary alkyl group and the other hydrocarbyl substituent can be a hydrocarbyl group such as, for example, an alkyl, cycloalkyl, cycloalkylalkyl, cycloalkenyl, aryl, aralkyl, or alkyl-substituted aryl group.

Among particularly preferred sterically hindered compounds are:
2,6-di-tert-butyl-4-methoxymethylphenol;
2,6-di-(1,1,2-trimethylpropyl)-4-methoxymethylphenol;
2-methyl-6-tert-butyl-4-methoxymethylphenol;
2-methyl-6-(1,1,2-trimethylpropyl)-4-methoxymethylphenol;
2-methyl-6-(1,1,3,3-tetramethylbutyl)-4-methyoxymethylphenol;
2,6-di-tert-butyl-4-acetoxymethylphenol;
2,6-di-(1,1,2-trimethylpropyl)-4-acetoxymethylphenol;
2-tert-butyl-5-methyl-4-acetoxymethylphenol;
2-methyl-6-(1,1,2-trimethylpropyl)-4-acetoxymethylphenol;
2-methyl-6-(1,1,3,3-tetramethylbutyl)-4-acetoxymethylphenol;
2,6-di-tert-butyl-4-hydroxymethylphenol;
2,6-di-(1,1,2-trimethylpropyl)-4-hydroxymethylphenol;
2-tert-butyl-6-methyl-4-hydroxymethylphenol;
2-methyl-6-(1,1,2-trimethylpropyl)-4-hydroxymethylphenol;
2-methyl-6-(1,1,3,3-tetramethylbutyl)-4-hydroxymethylphenol.

Of such particularly preferred compounds, 2,6-di-tert-butyl-4-methoxymethylphenol and 2,6-di-tert-butyl-4-acetoxymethylphenol are especially preferred for use as reactant (b).

Compounds of this Invention

In order to provide an indication of the types of compounds of this invention that can be made by use of the process technology of this invention, the following equations and structural formulas are presented in which, for purposes of illustration but not limitation, typical compounds of this invention producible from 2,6-di-tert-butyl-4-methoxymethylphenol and diphenyl monosulfide, or diphenyl disulfide are illustrated. It will be understood and appreciated that the invention is not limited to only the products produced from these particular reactants.

Reaction 1)

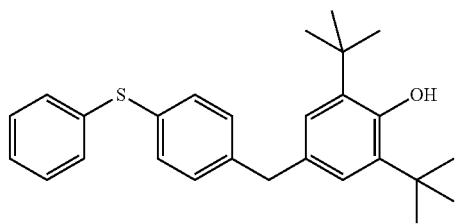

-continued

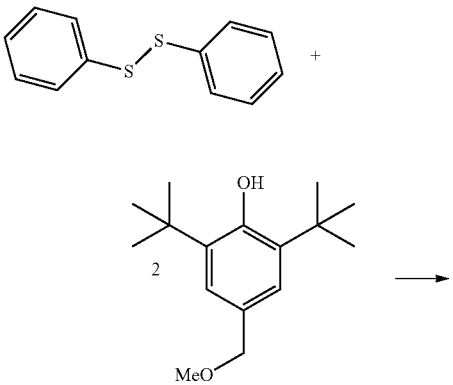

Reaction 2)

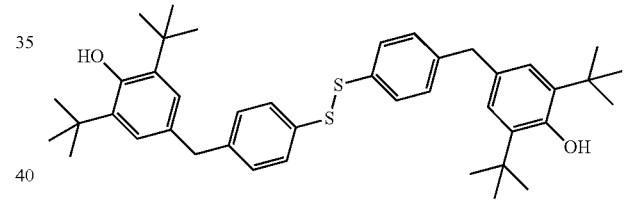

Reaction 3)

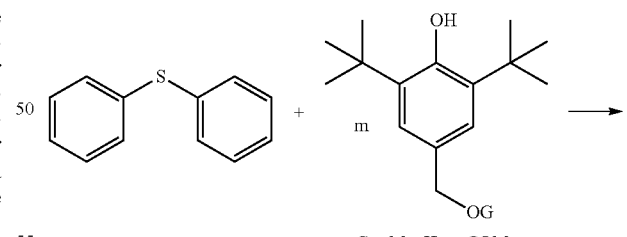

G = Me, H, or COMe

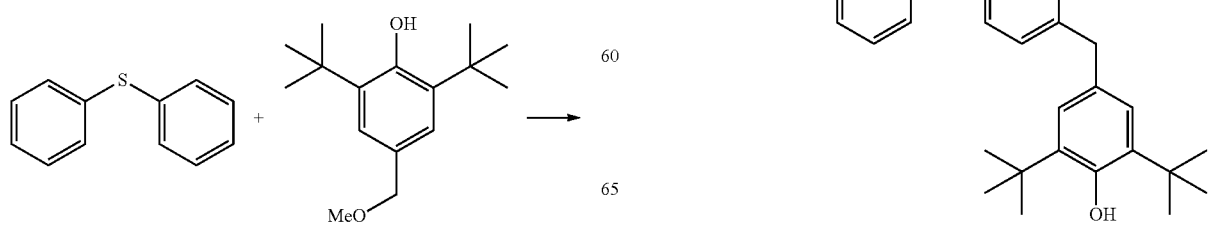

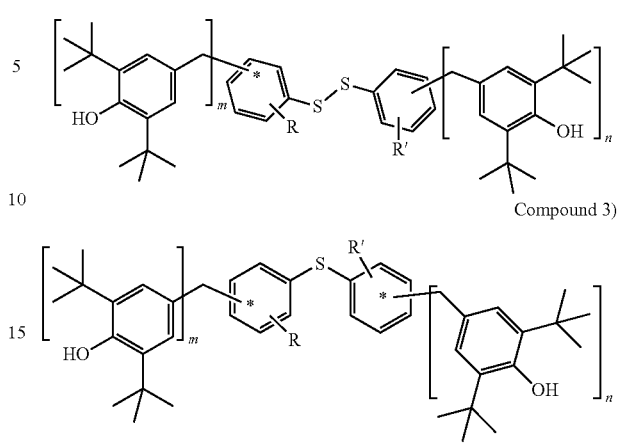

Compound 2)

Compound 3)

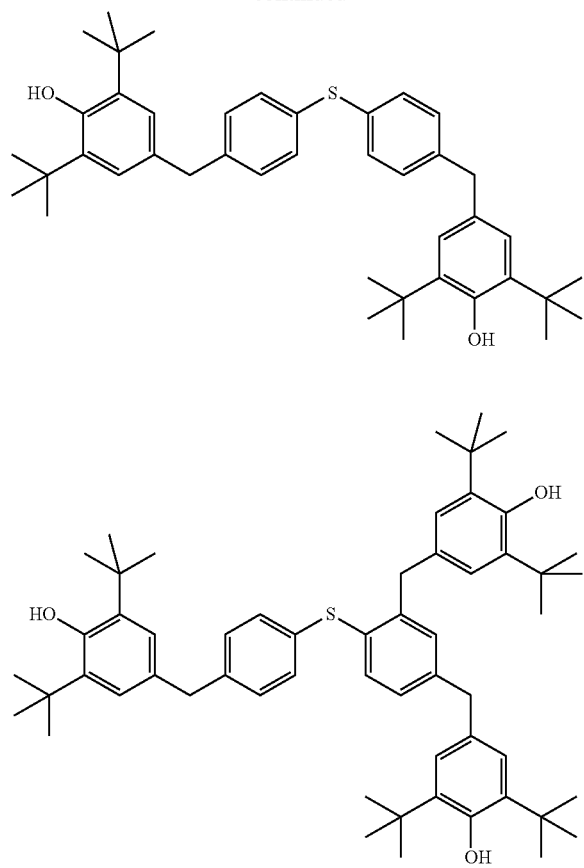

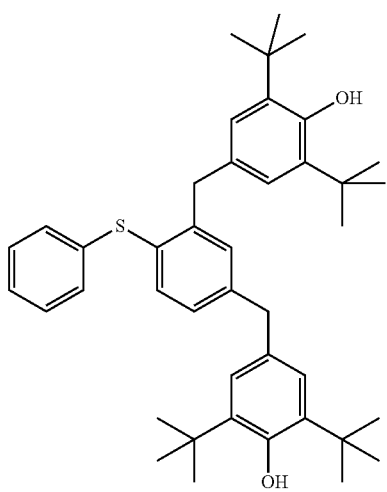

Compound 1)

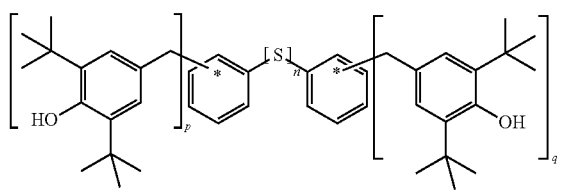

As can be seen, the formulas designated as Compound 1), Compound 2), and Compound 3) are really groups of compounds. Furthermore, since they include different designations from the preceding formulas, the definitions of R, R', p, q, m, and n are given here. In the formula of Compound 1), n is 1-6, preferably 1-2, and more preferably, 1; p is 1-5, preferably 1-4, more preferably 1-3, and still more preferably, 1-2; and q is, independently, 0-5, preferably 0-4, more preferably 0-3, and still more preferably 0-2.

In the formulas for Compounds 2) and 3), R and R' are substituents that can be the same or different from each other. Such substituents are selected from among inert hydrocarbyl, alkoxy, aryloxy, alkylthio, halo, amino, alkyl amino, or aryl amino (i.e., substituent groups which do not interfere with the reaction which forms the compounds of this invention). Also, in the formulas for Compounds 2) and 3), m is 0-4 and preferably 0-3, and more preferably, 0-2; and n is, independently, 1-4, preferably 1-3, and more preferably 1-2.

It will be understood that when a formula of Compound 1), Compound 2), or Compound 3) is an individual compound, the numbers designated by p, q, m, and n will be whole numbers. On the other hand, when a formula of Compound 1), Compound 2), or Compound 3) represents a mixture of compounds, the numbers designated by p, q, m, and n can be whole numbers or fractional numbers, and such fractional numbers can be less than 1.

As shown by reaction 1), the first product formed in the reaction between the diaryl monosulfide reactant (in the case illustrated, diphenyl monosulfide) and the 2,6-dihydrocarbyl-4-methoxymethylphenol (in the case illustrated, 2,6-di-tert-butyl-4-methoxymethylphenol) depicts the formation of a product having a single 3,5-dihydrocarbyl-4-hydroxybenzyl substituent bonded to one of the rings of the diaryl monosulfide reactant as the major product. Typically, when a large excess of diaryl monosulfide reactant is reacted with 2,6-dihydrocarbyl-4-methoxymethylphenol (in the case illustrated, 2,6-di-tert-butyl-4-methoxymethylphenol) a product having a single 3,5-dihydrocarbyl-4-hydroxybenzyl substituent bonded to one of the rings of the diaryl monosulfide reactant as the major product is produced and only minor quantities of disubstituted and trisubstituted compounds also coproduced. By use of equimolar or higher molecular ratios of the 2,6-dihydrocarbyl-4-methoxymethylphenol relative to the diaryl monosulfide reactant, additional 3,5-dihydrocarbyl-4-hydroxybenzyl moieties can be introduced into the rings of the diaryl monosulfide resulting in a mixture with multiple components that makes the product a liquid or low melting solid at room temperature.

Reaction 2) illustrates the facts that the arylsulfide reactant can contain more than one sulfur atom in the bridge (in the case illustrated, the disulfide reactant is diphenyl disulfide) and that by use of appropriate proportions both aryl groups of the diarylsulfide reactant can be substituted by one or more 3,5-dihydrocarbyl-4-hydroxybenzyl substituents.

Reaction 3) illustrates that the diarylsulfide reactant can react with one or more of the hindered phenolic reactant (b) to produce product mixtures that contain at least monosubstituted, di-substituted, and tri-substituted diarylsulfide. The composition of the final product depends largely upon the mole ratio of reactant (a) and (b) used.

Compounds of this invention produced using a poly (arylsulfide) as described above in connection with Formula (II) have at least one and typically a plurality of 3,5-dihydrocarbyl-4-hydroxybenzyl groups as substituents on various arylene groups of the repeating units of the oligomer or polymer. The amount of ring-substitution on the poly (arylsulfide), depends largely upon the mole ratio of reactants (a) and (b) used in the reaction. Preferred compounds of this invention adapted for use as antioxidant and antiwear agents for lubricants are formed from one or a mixture of poly(arylsulfides) and have a solubility in mineral oil of at least 10 grams per liter at 25° C.

Reaction Conditions

The compounds of this invention can be produced by a process which comprises forming a liquid reaction medium from:

a) at least one compound of formula (II):

$$R-S_n-[R-S-]_mR \quad \text{(II)}$$

wherein each R is, independently, an aromatic hydrocarbon group having in the range of 6 to about 24 carbon atoms, wherein m is a number in the range of 0 to about 20, wherein n is a number in the range of 1 to 6 when m is 0, and wherein m is in the range of 1 to about 20 when n is 1; and b) at least one sterically hindered 2,6-dihydrocarbylphenol having in its 4-position a methoxymethyl group, a carboxymethyl group, or a hydroxymethyl group;

in the presence of an acidic alkylation catalyst, and causing or enabling reaction to occur so that one or more compounds of this invention (typically a mixture of two or more compounds of this invention) are formed. Reaction is typically performed at reaction temperatures in the range of about 25 to about 130° C.

The reaction between reactants (a) and (b) is typically conducted in a reaction solvent. Non-limiting examples of suitable solvents which can be used include halogenated solvents like dichloromethane, chloroform, and bromochloromethane, ketones like acetone and methyl ethyl ketone, hydrocarbons like toluene and xylene, alcohols like methanol and butanol and carboxylic acids like acetic acid and propanoic acid.

Mineral acid catalysts such as sulfuric acid or phosphoric acid, or an organic acid such as alkylsulfonic acid, or a solid acid catalyst such as Amberlyst® catalyst or a zeolite is used to catalyze the reaction. The makeup of the product depends largely upon the ratio between the moles of reactant (b) to the number of reactive sites on reactant (a), which reactive sites will be readily apparent to one of ordinary skill in the art. Conventional work-up procedures can be used for separating and recovering purified product. Typically, the reaction product, when in liquid or oily form, is freed of any solids by use of conventional liquid-solids separation procedures, such as centrifugation, filtration, or by dilution with a liquid diluent followed by liquid phase separation. The product can be washed one or more times with an aqueous washing solution or the reaction mixture can be introduced into a body of heated water in order to drive off the solvent and other volatile impurities that may be present. In cases where the product is primarily in solid form, the solids are typically introduced into a large body of hot water in order to remove the entrapped solvent. These and other methods of product work-up will be apparent to those of skill in the art.

When it is desired to isolate one or more multi-ring functionally substituted aromatic compounds present in the overall reaction product, use may be made of solvent extraction, distillation conducted at reduced pressures, if necessary, or chromatographic separation procedures.

Measurement of Deposits and Volatiles in TEOST-MHT

The following procedure is used to determine the measurement of deposits and volatiles in a formulated oil using the TEOST MHT instrument test. The TEOST MHT instrument should be run according to the ASTM D 7097 method and manufacturer specifications. The test involves passing a thin film of test engine oil over a heated wire-wound depositor rod with the aide of a precision pump.

A test rod is heated at 285° C. and the test run for 24 hours. The thin film of oil moves evenly down the rod and is collected at the flow out point of the test assembly apparatus. Recovered oil is circulated back to the depositor rod via the precision pump. During the 24 hour test period volatiles are produced that flash off the hot rod surface and condense on the glass mantle of the test assembly apparatus. These volatiles are recovered at the volatiles out port of the test assembly and are collected in a glass vial. At the end of the test, deposits are determined by the increase in depositor rod weight and reported in milligrams (mg). The collected volatiles are accurately weighed and reported in grams (g).

The method requires a number of independent calibrations, including for example, calibrating the air flow rate, the oil pump rate, the temperature controller settings, and the control thermocouple. The method also requires running certified reference oils periodically to determine the severity of the test. For example, a certified medium deposit reference oil should produce approximately 40-60 mg of deposits, while a certified high deposit reference oil should produce approximately 70-90 mg of deposits. It is understood that a severe test condition will usually produce heavier deposits and higher levels of volatiles. On the other hand, a mild test condition will usually produce lighter deposits and much lower levels of volatiles. Engine oils that perform well, i.e. low deposits and low volatiles, under a severe test condition are expected to perform even better under a mild test condition. However, engine oils that perform well under a mild test condition are expected to perform worse under a severe test condition. The additive combination of this invention gives excellent deposit control and reduced volatiles formation under both severe and mild conditions. The robust performance of the new additive combination under both severe and mild test conditions is another advantage of this invention.

A fully formulated oil (about 8-9 g) and antioxidant composition (about 0.06-0.12 g) are added to a flask equipped with a Teflon stirring bar and stirred for 20-60 minutes without heating. The depositor rod, sample flask, oil inlet, air inlet, and volatiles collection vial are fitted to the TEOST apparatus according to manufacturers specifications. The pump is started at a high flow rate and run until the test oil reaches the connection of the pump and oil feed tube, at which point the pump flow is turned to zero. The heater switch is turned on and when the depositor rod temperature controller is between 200-210° C., the pump speed increased to achieve a sample delivery of 0.25±0.02 g/min, making sure that the oil is flowing down the depositor rod and is not leaking. The temperature is allowed to stabilize at 285±2° C. and the test is run under these conditions for 24 hrs.

Three test tubes are prepared with cyclohexane or another suitable hydrocarbon solvent for extraction of oil from the depositor rod. The test instrument is disassembled as per manufacturer's instructions and the depositor rod is transferred to a weighing boat and kept under cover. The depositor rod is placed successively for 10 minutes each in each of the three test tubes prepared with a hydrocarbon solvent. The rod is placed in tared weighing boat and allowed to sit for 10 minutes to insure evaporation of the hydrocarbon solvent. The rod and the boat are weighed, verifying that a constant mass has been achieved. The contents of the three test tubes, along with the lower-end cap deposits and glass mantle deposits, are washed into a common container which is then filtered using a glass funnel equipped with a filter cartridge. After completing the filtering, the filter cartridge is dried under vacuum and weighed, until a constant mass is achieved. The total mass of the deposits from the depositor rod and filter deposits is then determined.

During the 24 hour duration of the test, the volatile compounds in the formulated oil that are there originally or those formed during the test, are flashed off the depositor rod. These volatiles condense on the glass mantle and are collected on a continuous basis in a small, weighed vial. The vial and volatiles are measured at the end of the 24 hour test period and the amount of volatiles is calculated by subtracting the original weight of the vial.

Oxidation Induction Test

The antioxidant effectiveness of the compounds or composition of the invention was shown by use of a standardized oxidation induction test procedure (ASTM D 6186) in which a lubricating oil containing a specified amount of an additive is subjected to oxidation in a heated pressure-resistant vessel at a temperature of 160° C. charged with oxygen under an initial elevated pressure of 500 psig. The longer the induction time (OIT) before a pressure drop occurs, the more stable is the composition. In this test, antioxidant compositions were blended with EHC 60 oil (a mineral base oil having a kinematic viscosity at 100° C. of 6.1 cSt, a viscosity index of 114, and a Noack volatility of 8 wt %; ExxonMobil) and the resultant blend was subjected to the above oxidation induction test procedure.

The following examples are presented for the purposes of illustration. They are not intended to impose limits on the overall scope of the invention. In these examples, the substituents referred to in connection with the mixture of products formed in the reaction are 3,5-di-tert-butyl-4-hydroxybenzyl substituents.

EXAMPLE 1

Diphenyl sulfide and 2,6-di-tert-butyl-4-methoxymethylphenol, 1:2 mole ratio: Diphenyl sulfide (0.1 mol, 18.6 g) was dissolved in dichloromethane (150 mL) and sulfuric acid (80%, 10 mL) was added and the mixture was stirred at room temperature. A solution of 2,6-di-tert-butyl-4-methoxymethylphenol (0.2 mol, 50 g) in dichloromethane (110 mL) was added at 40° C. over a 40 minutes period. After stirring the reaction mixture at 40° C. for four hours the organic solution was washed with water (2×100 mL) and dried over magnesium sulfate. Evaporation of solvent under reduced pressure afforded a thick oil. LC-Mass analysis showed mono-substituted product (30%), di-substituted product (35%), tri-substituted product (9%), 4,4'-methylenebis(2,6-di-tert-butylphenol) (11%), unreacted diphenyl sulfide (11%), and higher oligomers (4%). Pressurized Differential Scanning calorimetry (PDSC) showed an OIT of 78 minutes (0.25 wt %), 101 minutes (0.5 wt %), and 113 minutes (0.75 wt %).

The Oxidation Induction Time (OIT) determination for product of this Example was conducted as follows: Three lubricant formulations were prepared as by blending 0.25 wt %, 0.50 wt % and 0.75 wt % of the product of Example 1 in EHC 60 oil as described earlier. These blends were subjected to the test conditions of ASTM D 6186, except that a temperature of 160° C. was used. The oxidation induction times were 78, 101, and 113 minutes, for 0.25 wt %, 0.50 wt %, and 0.75 wt % blends, respectively.

EXAMPLE 2

Diphenyl sulfide and 2,6-di-tert-butyl-4-methoxymethylphenol, 1:3 mole ratio: The same procedure as in Example 1 was followed except for the amount of 2,6-di-tert-butyl-4-methoxymethylphenol that was increased to 75 g (0.3 mol). Analysis of the crude showed unreacted diphenyl sulfide (9%), mono-substituted product (27%), di-substituted product (31%), tri-substituted product (8%), 4,4'-methylenebis(2,6-di-tert-butylphenol) (19%). PDSC showed OIT of 96 minutes (0.25 wt %), 110 minutes (0.5 wt %), and 126 minutes (0.75 wt %).

EXAMPLE 3

Diphenyl sulfide and 2,6-di-tert-butyl-4-methoxymethylphenol, 1:2 mole ratio: Diphenyl sulfide (0.03 mol, 5.6 g) and 2,6-di-tert-butyl-4-methoxymethylphenol (0.06 mol, 15 g) were suspended in acetic acid (70 mL) at room temperature and stirred under nitrogen. Sulfuric acid (0.98 g of 98%) was added to the mixture and heated the resulting solution to 70° C. and kept at this temperature for 6 hours. The reaction mixture was cooled down to room temperature and diluted with heptane (130 mL). The organic solution was washed with water (2×100 g) and dried by azeotropic distillation. Concentration under reduced pressure at 70° C. afforded a viscose oil that became a glassy solid at room temperature. LC analysis showed diphenyl sulfide (8%), mono-substituted product (27%), di-substituted product (39%), tri-substituted product (9%), 4,4'-methylenebis(2,6-di-tert-butylphenol) (4%), and higher oligomers (13%).

EXAMPLE 4

Diphenyl sulfide and 2,6-di-tert-butyl-4-methoxymethylphenol, 1:3 mole ratio: Diphenyl sulfide (0.06 mol, 11.2 g) and 2,6-di-tert-butyl-4-methoxymethylphenol (0.18 mol, 45 g) were suspended in acetic acid (140 mL) at room temperature and stirred under nitrogen. Sulfuric acid (2 g of 98%) was added to the mixture and heated the resulting solution to 70° C. and kept at this temperature for 6 hours. The reaction mixture was cooled down to room temperature and diluted with heptane (130 mL). The organic solution was washed with water (2×100 g) and dried by azeotropic distillation. Concentration under reduced pressure at 70° C. afforded a viscose oil that became a glassy solid at room temperature. LC analysis showed diphenyl sulfide (5%), mono-substituted product (22%), di-substituted product (40%), tri-substituted product (11%), 4,4'-methylenebis(2,6-di-tert-butylphenol) (9%), and higher oligomers (13%).

It will be seen that the products formed in the above Examples comprised (a) diphenyl monosulfide substituted at least by one 3,5-di-tert-butyl-4-hydroxybenzyl moiety, (b) diphenyl monosulfide substituted by two 3,5-di-tert-butyl-4-hydroxybenzyl moieties, and (c) diphenyl monosulfide substituted by three 3,5-di-tert-butyl-4-hydroxybenzyl moieties and (d) diphenyl monosulfide substituted by more than three 3,5-di-tert-butyl-4-hydroxybenzyl moieties.

EXAMPLE 5

2,6-Di-tert-butyl-4-methoxymethylphenol (0.1 g) was dissolved in diphenyl disulfide (1 g) at room temperature under nitrogen. One drop of methanesulfonic acid was added and stirred at room temperature. Analysis showed more than 90% of the mono-substituted product.

Substitution of equivalent amounts of 2-tert-butyl-6-methyl-4-methyoxymethylphenol for the 2,6-di-tert-butyl-4-methoxymethylphenol in the processes of Examples 1-4 results in the formation of similar product mixtures in which the alkyl groups in the ortho positions relative to the hydroxyl group of the substituents are tertiary butyl and methyl.

EXAMPLE 6

Diphenyl sulfide (0.1 mol, 18.6 g) and half of the total amount of 2,6-di-tert-butyl-4-methoxymethylphenol (0.25 mol, 69.4 g) to be used were mixed in acetic acid (180 g) at room temperature under nitrogen. Sulfuric acid (2.94 g, 98%) was added to the mixture at room temperature, and then the mixture was heated to 80° C. After one-half hour at these conditions, the rest of 2,6-di-tert-butyl-4-methoxymethylphenol was added and heating continued at 80° C. for another 5.5 hours. After cooling the mixture to ambient temperature, heptane (200 mL) was added and the organic solution was washed with water (3×150 g) and then dried by azeotropic distillation. The resulting dry solution was stripped under reduced pressure and then the residue was subjected to vacuum (2-3 mmHg) at 70° C. for one hour. The resulting orange glassy solid was analyzed by GPC, which showed 6.4% unreacted diphenyl sulfide, 24.5% mono-substituted, 36.2% di-substituted, 9.6% tri-substituted diphenyl sulfide, 3.3% of 4,4'-methylenebis(2,6-di-tert-butylphenol), and 18.8% of oligomeric unidentified products.

EXAMPLE 7

Measurement of Deposits by TEOST-MHT:

Two lubricant formulations were prepared by blending 0.75 wt % and 1.25 wt % of product of Example 6 in a fully formulated base oil. These formulations were subjected to the test conditions described above. An average deposit of 49.0 mg and 43.9 mg were measured for 0.75 wt % and 1.25 wt % blends, respectively.

Uses of Compounds of this Invention

The compounds of this invention can be utilized as antioxidants (oxidation inhibitors) for a wide variety of substrates normally susceptible to oxidative degradation over time, especially when exposed to elevated temperatures. In addition, the compounds of this invention can be utilized as multifunctional additives for lubricant compositions, in that the compounds of this invention can serve both as antioxidants and as antiwear agents. Thus, they are well suited for use as additives to natural and synthetic engine oils, gear oils, automatic transmission fluids, machine lubricants, and similar oils of lubricating viscosity which are subjected to extreme pressures during use.

The compounds of this invention—whether in the form of (i) individual isolated compounds, (ii) mixtures of two or more isolated individual compounds, or (iii) mixtures comprised of products formed by reaction of reactants (a) and (b) and which mixtures after work-up of the reaction product mixture contain no more than about 1 wt % of reaction solvent and catalyst residues—can be made available for use or sale as "neat" compositions for use as an antioxidant in any organic substrate material normally susceptible to oxidative deterioration in the presence of air or oxygen. In this usage, an antioxidant quantity of a compound of this invention can be blended with the substrate such as, for example, a lubricating oil; a liquid fuel; a thermoplastic polymer, resin or oligomer; or a natural or synthetic rubber or elastomer.

Additive compositions of this invention constitute another way of protecting such organic material against premature oxidative deterioration in the presence of air or oxygen. Thus, when adapted for use as an additive in oils, one or more compounds of this invention—whether in the form of (i) individual isolated compounds, (ii) mixtures of two or more isolated individual compounds, or (iii) mixtures comprised of products formed by reaction of reactants (a) and (b) and which mixtures after work-up of the reaction product mixture contain no more than about 1 wt % of reaction solvent and catalyst residues—can be partially diluted or dissolved in a base oil or process oil, or can be blended with other components that are commonly used in a wide variety of lubricants. Examples of base oils that may be used include Group I, II, and III mineral oils, poly-alpha-olefins, synthetic esters, gas to liquid derived oils and bio-based oils. Examples of other additives that may be used to produce new and useful lubricant additive blends with the compounds of this invention include, but are not limited to, dispersants, detergents, anti-wear additives, extreme pressure additives, corrosion inhibitors, rust inhibitors, friction modifiers, pour point depressants, viscosity index modifiers, emulsifiers, demulsifiers, seal swell agents, solubilizing agents, antifoam agents, acid scavengers, metal deactivators, and other antioxidants or stabilizers. Combinations of one or more of these components can be used to produce additive blends with one or more of the compounds of this invention.

Also, additive compositions for use in internal combustion engine oils, railroad and marine lubricants, natural gas engine oils, gas turbine oils, steam turbine oils, aviation turbine oils, rust and oxidation oils, hydraulic fluids, compressor fluids, slideway oils, quench oils, manual and automatic transmission fluids, gear oils, greases, etc. can be formed by blending one or more of the compounds of this invention with a diluent, solvent, or carrier fluid and/or one or more other suitable additives.

The additive compositions of this invention adapted for use in oils can contain in the range of 5 wt % to 95 wt % based on the total weight of the antioxidant composition of an antioxidant product of this invention, the specific amount used depending upon such factors as the number and type of other components in the blend, and the use to which the blend is to be put. Finished lubricating oils of this invention will contain an antioxidant quantity of a compound of this invention, which amount typically is at least about 0.1 wt %, preferably at least about 1 wt %, and more preferably at least about 3 wt %, based on the total weight of the finished lubricating oil. Depending upon the type of service for which the oil of lubricating viscosity is intended, the amount of the compound of this invention blended therein either as a sole additive or as an additive composition containing one or more other components will typically be no more than about 15 wt %, on the same basis.

The lubricating oil used in these embodiments of the present invention can be mineral, synthetic, or a blend of mineral and/or synthetic lubricating oils. These oils are typical industrial or crankcase lubrication oils for gas or steam turbines, transmission or hydraulic fluids, spark-ignited and compression-ignited internal combustion engines, for example natural gas engines, automobile and truck engines, marine, and railroad diesel engines. Mineral lubricating oils can be refined from aromatic, asphaltic, naphthenic, paraffinic or mixed base crudes. The lubricating oils can be distillate or residual lubricating oils, such as for example, bright stock, or blends of the oils to give a finished base stock of desired properties. Synthetic base oils used can be (i) alkyl esters of dicarboxylic acids, polyglycols and alcohols, (ii) poly-alpha-olefins, including polybutenes, (iii) alkyl benzenes, (iv) organic esters of phosphoric acids, or (v) polysilicone oils. The base oil typically has a viscosity of about 2 to about 15 cSt and preferably about 2.5 to about 11 cSt at 100° C.

Additive compositions adapted for use in forming liquid fuel compositions of this invention (e.g., gasolines, diesel fuels, jet fuels, gas turbine engine fuels, etc.) can be formed by blending therewith or providing therein an antioxidant quantity of one or more of the compounds of this invention in the form of an additive composition of this invention comprising at least one novel compound of this invention together with one or more other additives, such as detergents, carrier fluids, demulsifiers, corrosion inhibitors, metal deactivators, lubricity agents, pour point depressants, cetane or octane improvers, antiknock agents, anti-icing agents, etc. The substrate fuels can be derived from petroleum or can be synthetic fuels, or they can be blends of both such types of materials. The amount of these new compositions in an additive blend of this invention can vary from 5 wt % to 95 wt %, based on the total weight of the additive blend, depending on the type and number of other components in the blend.

Liquid fuel compositions of this invention are typically formed by blending an antioxidant quantity of at least one of the compounds of this invention with the fuel, either as a single additive composition (i.e., containing no other type(s) of fuel additive) or as an additive concentrate comprised of at least one of the compounds of this invention together with at least one other type of fuel additive. The additive concentrates of this invention thus can contain in the range of about 5 to about 95 wt % of at least one of the compounds of this invention, with the balance to 100 wt % being one or more other additives and optionally, a diluent, solvent or carrier fluid, all based on the total weight of the additive concentrate. The finished fuel compositions typically contain an antioxidant quantity in the range of about 0.0001 to about 0.1 wt %, and preferably in the range of about 0.001 to about 0.05 wt % of at least one of the compounds of this invention, all based on the total weight of the finished fuel composition.

It will of course be understood that on blending one or more of the compounds of this invention with a liquid substrate fuel or oil, the compounds of this invention may no longer exist in exactly the same composition and form as they were upon addition to such substrate fuel or oil. For example, they may interact with one or more of the other components in the fuel or oil and/or they may complex with or otherwise change by virtue of becoming dissolved in the substrate fuel or oil. However, since the finished fuel or lubricant possess antioxidant properties because of the addition thereto of the one or more compounds of this invention, the possibility of such transformations upon dilution in the substrate matters not. What matters pursuant to this invention is that whatever is formed upon such dilution is effective as an antioxidant. Consequently, expressions such as "containing in the range of", "in", etc. with reference to at least one of the compounds of this invention are to be understood as referring to the at least one of the compounds of this invention as it existed just prior to being blended or mixed with any liquid fuel or base oil and/or with any other component.

It will also be understood that the amount of the compounds of this invention in a finished lubricant will vary depending upon the lubricant type, the identity of the one or more compounds of this invention being used, and the desired level of performance required. For example, in a turbine oil, levels of the product(s) of this invention often vary from about 0.05 to about 1.0 wt %, based on the total weight of the finished turbine oil. However, in an engine oil, levels typically vary from about 0.2 to about 2 wt %, based on the total weight of the engine oil. In low phosphorus engine oils, levels may vary from about 0.3 to about 3 wt %, based on the total weight of the low phosphorus engine oil. In phosphorus-free engine oils levels may be as high as about 4 or 5 wt %, based on the total weight of the phosphorus-free engine oil. It will be understood that all wt. % are based on the total weight of the finished oil containing all additives, etc. When used properly the compounds of this invention serve as antioxidant compositions. Thus, this invention also provides novel improved methods of reducing oxidation, reducing viscosity increase and polymerization, reducing acid formation and retaining lubricant basicity (TAN and TBN), reducing varnish and deposit formation, reducing friction and wear, reducing dependence on zinc dialkyldithiophosphate (ZDDP) and phosphorus for oxidation and deposit control, extending the usable life of all lubricant mentioned above, and reducing oil changes and vehicle maintenance. In each of such methods, a lubricant composition of this invention comprising an oil of lubricating viscosity with which has been blended an antioxidant quantity of at least one novel compound of this invention is utilized as the lubricant. Still another method of this invention is a method of improving the oxidation stability of a lubricating oil, wherein said method comprises blending with a lubricating oil an oxidation stability improving amount of at least one compound of this invention. In this way the oxidation stability of the oil is significantly improved, as compared to the same oil devoid of a compound of this invention.

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with ordinary skill of a chemist, is thus of no practical concern.

Except as may be expressly otherwise indicated, the article "a" or an if and as used herein is not intended to limit, and should not be construed as limiting, a claim to a single element to which the article refers. Rather, the article "a" or an if and as used herein is intended to cover one or more such elements, unless the text expressly indicates otherwise.

The invention may comprise, consist or consist essentially of the materials and/or procedures recited herein.

This invention is susceptible to considerable variation in its practice. Therefore the foregoing description is not intended to limit, and should not be construed as limiting, the invention to the particular exemplifications presented hereinabove.

That which is claimed is:

1. A composition which comprises organic material normally susceptible to oxidative degradation in the presence of air or oxygen with which material has been blended a multi-ring antioxidant product in an amount sufficient to inhibit such oxidative degradation, wherein the organic material is an oil of lubricating viscosity or a liquid fuel composition, and wherein the multi-ring antioxidant has the formula

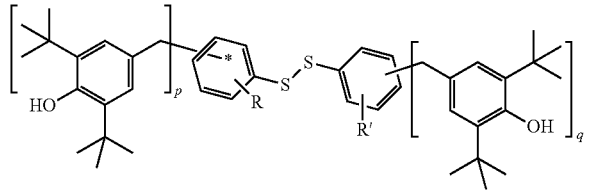

wherein:

R and R' are selected from hydrogen atoms, hydrocarbyl, alkoxy, aryloxy, alkylthio, halo, amino, alkyl amino, or aryl amino substituent groups which do not interfere with the reaction which forms the compounds of this invention;

p is 0-4; and q is, independently, 1-4.

2. A composition as in claim 1 in which the antioxidant is in the liquid state at one or more temperatures below 100° C.

3. A composition as in claim 1 wherein said organic material is an oil of lubricating viscosity.

4. A composition as in claim 1 wherein said organic material is a liquid fuel composition.

5. A composition as in claim 1 wherein R and R' are hydrogen atoms.

6. The composition of claim 1, wherein p is 0-2.

7. The composition of claim 6, wherein p is 1.

8. The composition of claim 1, wherein q is 1-2.

9. The composition of claim 8, wherein q is 1.

10. The composition of claim 1, wherein R and R' are each hydrocarbyl.

11. The composition of claim 1, wherein the multi-ring antioxidant has the formula of:

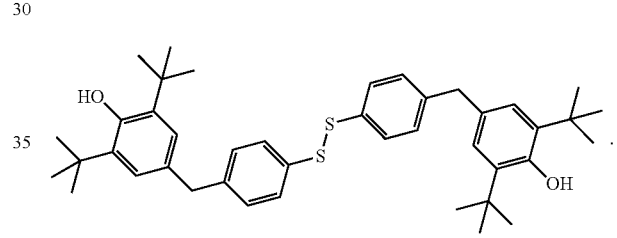

* * * * *